United States Patent
Katayama et al.

(10) Patent No.: US 6,586,065 B1
(45) Date of Patent: Jul. 1, 2003

(54) CAPILLARY HAVING COATED INNER WALL

(75) Inventors: Hiroyuki Katayama, Ibaraki (JP); Yasushi Ishihama, Ibaraki (JP)

(73) Assignee: Eisai Co., Ltd., Tokyo (JP)

( * ) Notice: Subject to any disclaimer, the term of this patent is extended or adjusted under 35 U.S.C. 154(b) by 0 days.

(21) Appl. No.: 09/319,043

(22) PCT Filed: Dec. 3, 1997

(86) PCT No.: PCT/JP97/04422

§ 371 (c)(1),
(2), (4) Date: Jun. 1, 1999

(87) PCT Pub. No.: WO98/25137

PCT Pub. Date: Jun. 11, 1998

(30) Foreign Application Priority Data

Dec. 3, 1996 (JP) .............................................. 8-323021

(51) Int. Cl.$^7$ .............................................. G01N 27/26
(52) U.S. Cl. ..................... 428/36.9; 428/34.7; 428/420; 204/454; 156/272.2; 156/278
(58) Field of Search ............................... 428/34.7, 36.9, 428/420; 156/272.2, 278; 204/454

(56) References Cited

U.S. PATENT DOCUMENTS

| 5,015,350 A | * | 5/1991 | Wiktorowicz ............ 204/180.1 |
| 5,208,111 A | * | 5/1993 | Decher et al. ............... 428/420 |
| 5,502,169 A | * | 3/1996 | Schomberg et al. ........ 204/454 |

FOREIGN PATENT DOCUMENTS

| JP | A5503989 | 6/1993 |
| JP | A5288717 | 11/1993 |
| JP | A7507876 | 8/1995 |
| JP | A8508577 | 9/1996 |

* cited by examiner

Primary Examiner—Harold Pyon
Assistant Examiner—Sow-Fun Hon
(74) Attorney, Agent, or Firm—Birch, Stewart, Kolasch & Birch, LLP

(57) ABSTRACT

It is to provide a capillary having adsorbed a polymer.

A capillary having absorbed on an inner wall of the capillary, an ionic polymer having positive electric charge and an ionic polymer having negative electric charge alternately, and a process for producing the same.

11 Claims, 4 Drawing Sheets

CZE under an acidic condition

Conditions
Buffer : Phosphate pH 2.75
V : +7kV
Capillary: uncoated 27 cm (20 cm effective length)
ML coated 27 cm (20 cm effective length)

Electrosmosis flows of a capillary having a non-treated and a coated inner wall

Capillary: 27cm(20 cm effective length)
uncoated : eo    + ⟹ −
LPA      : eo    suppressed
PB       : eo    − ⟹ +
ML       : eo    + ⟹ −

⊚ : LPA is a typical commercially available coated capillary and the electrosmosis flow is suppressed throughout all the pH vakyes.

MEKC under an acidic condition

Conditions
Buffer : 50 mM SDS in phosphate pH 2.75
V : +7 kV
Capillary: ML coated 27 cm (20 cm effective length)

The measurement of pKa of Trp by a capillary electrophoresis method

Conditions
Buffer : Phosphate pH 3.10 (I=0.05)
Capillary: uncoated 27 cm(20 cm effective length)
ML coated 27 cm (27 cm effective length)

CAPILLARY HAVING COATED INNER WALL

This application is the national phase under 35 U.S.C. §371 of PCT International Application No. PCT/JP97/04422 which has an International filing date of Dec. 3, 1997, which designated the United States of America.

BACKGROUND OF THE INVENTION

1. Field of Industrial Application

The present invention relates to a capillary having adsorbed a polymer, and a process for producing the same.

2. Prior Art

Capillary electrophoresis (hereinafter sometimes called as CE) is a generic name of electrophoresis conducted in a capillary having an inner diameter of 100 μm or less. The CE has characteristic features, such as super high resolving power (number of theoretical plates: 100,000 to 10,000,000), high speed analysis, a minute amount of sample (several nl), the use of an aqueous solvent, possibility of capillary on-line detection, and the like. By utilizing these characteristic features, the CE is used in various fields, such as measurement of drugs, foods and environmental substances. Among these, analysis of proteins can be exemplified as a filed that has a possibility of further development by the CE. However, it is considered that hydrophobic silicon and a polar silanol group are present on an inner wall of a capillary, and therefore in analysis of proteins by the CE, tailing of peaks or irreversible adsorption of a solute on the wall are often found due to an ionic mutual interaction and a hydrophobic interaction between the solute and the inner wall of the capillary. As a solution thereof, a capillary having an inner wall coated with a hydrophilic substance is employed.

The capillaries having a coated inner wall known at the present time have many problems, such as lack of stability, difference among lots, an insufficient adsorption preventing function, a high cost, and the like, and a technique for solving these problems is further demanded.

DISCLOSURE OF THE INVENTION

The invention relates to (1) a capillary having adsorbed on an inner wall of the capillary, an ionic polymer having positive electric charge and an ionic polymer having negative electric charge alternately, (2) a capillary having adsorbed on an inner wall of the capillary, an ionic polymer having positive electric charge and an ionic polymer having negative electric charge alternately, the innermost layer being the ionic polymer having positive electric charge, (3) a capillary having adsorbed on an inner wall of the capillary, an ionic polymer having positive electric charge and an ionic polymer having negative electric charge alternately, the innermost layer being the ionic polymer having negative electric charge, (4) a process for producing a capillary characterized by making the capillary adsorb, on an inner wall of the capillary, an ionic polymer having positive electric charge and an ionic polymer having negative electric charge alternately, (5) a process for producing a capillary, in the process for producing a capillary described above, comprising the step of firstly rinsing the capillary with a strong alkali solution before making it adsorb the ionic polymer having positive electric charge.

The capillary according to the present invention means a capillary for capillary electrophoresis, a capillary for connecting in gas chromatography and mass spectrometry, and the like, and can be applied to an infusion analysis of mass spectrometry and capillary electrophoresis/mass spectrometry.

The material of the capillary is generally fused quartz glass, and the inner diameter is generally from 50μ to 100μ.

The ionic polymer having positive electric charge in the present invention means a polymer having positive electric charge that is dissolved in water or an aqueous organic solvent, such as methanol, ethanol, acetonitrile, etc., and specifically, polybrene, chitosan, diethylaminoethyldextran, polyethyleneimine, etc. can be exemplified. These substances are generally used singly, but may be used in combination. Furthermore, different substances may be used in respective layers.

The ionic polymer having negative electric charge in the present invention means a polymer having negative electric charge that is dissolved in water or an aqueous organic solvent, such as methanol, ethanol, acetonitrile, etc., and specifically, dextran sulfate, heparin, heparin sulfate, hyaluronic acid, chondroitin sulfate, keratan sulfate, polygalacturonic acid, arginic acid, teikronic acid, etc. can be exemplified. These substances are generally used singly, but may be used in combination. Furthermore, different substances may be used in respective layers.

In the capillary according to the present invention, when the ionic polymer having positive electric charge and the ionic polymer having negative electric charge are adsorbed alternately in the same number of times, the innermost layer (the layer in contact with an electrophoretic solution) is the ionic polymer having negative electric charge, and when the number of times of adsorption of the ionic polymer having positive electric charge is larger than that of the ionic polymer having negative electric charge by once, the innermost layer is the ionic polymer having positive electric charge. In general, the ionic polymer having positive electric charge and the ionic polymer having negative electric charge each are coated once alternately, or the ionic polymer having positive electric charge, the ionic polymer having negative electric charge and then the ionic polymer having positive electric charge are coated alternately in this order, but both of the layers may be coated alternately twice or more.

Upon producing the capillary according to the present invention, in the case where the ionic polymer having positive electric charge and the ionic polymer having negative electric charge each are coated once alternately, it can be produced in such a manner that the capillary is rinsed with 1N sodium hydroxide and then water, and then after rinsing with the ionic polymer having positive electric charge of a low concentration, the capillary is rinsed with the ionic polymer having positive electric charge of a high concentration, followed by immediately rinsing with the ionic polymer having negative electric charge of a high concentration.

A capillary having adsorbed two or more layers of the ionic polymers can be produced by repeating the operation described above except for the rinse with 1N sodium hydroxide and the subsequent rinse with water. The rinse with 1N sodium hydroxide may be conducted with other strong alkali solutions, such as potassium hydroxide, etc.

The concentration of the ionic polymer having positive electric charge of a low concentration, which cannot be determined unconditionally as is different depending on the species of the ionic polymer, generally means a low concentration within a concentration range in that an electrosmosis flow does not largely depend on the concentration of the ionic polymer, and is, for example, from 0.1 to 0.5%, and preferably about 0.4%, for polybrene. The ionic polymer having positive electric charge of a high concentration means a high concentration within a concentration range in that an electrosmosis flow does not largely depend on the concentration of the ionic polymer, and is, for example, from 3 to 10%, and preferably from 5 to 10%, for polybrene.

The concentration of the ionic polymer having negative electric charge of a high concentration is preferably as high concentration as possible as far as it is soluble in a solvent, but since the viscosity of the solvent is generally increased at a high concentration to make rinsing difficult, the concentration is determined on balance between them, and is generally from 1 to 5%. For example, it is about 2% for dextran sulfate and is about 3% for heparin.

Figure 1:
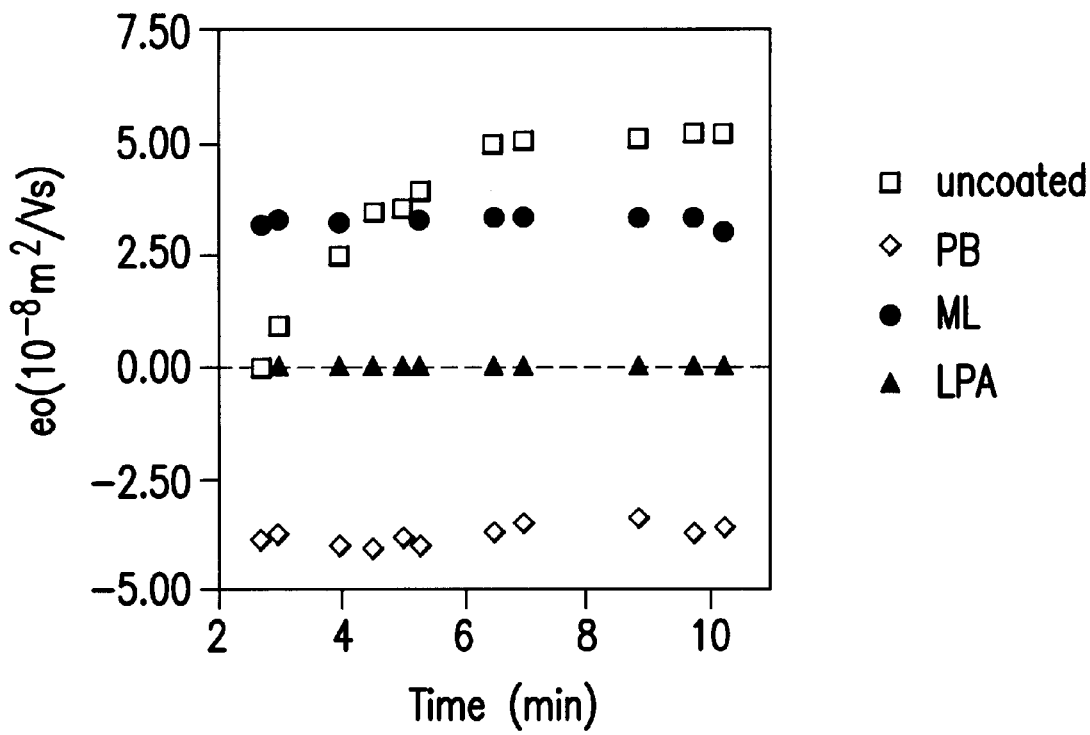
FIG. 1 is a graph showing electrosmosis flows of a capillary having a non-treated inner wall and a capillary having a coated inner wall. ML means the capillary according to the present invention, and uncoated means the capillary having no coating used as control.

Because a capillary having a non-treated inner wall, which has been conventionally used, has a silanol group on the inner wall, the electrosmosis flow depends on dissociation of the silanol group. The lower the pH of the electrophoretic solution is, the smaller the electrosmosis flow is due to suppress of dissociation of the silanol group, and it is substantially terminated at pH 3 or less (symbol of white square in FIG. 1). The capillary according to the present invention having, for example, dextran sulfate coated as the innermost layer has an electrosmosis flow that is independent on the pH of the electrophoretic solution (symbol of black circle in FIG. 1). In the commercially available coated capillary, represented by an LPA coated capillary, the electrosmosis flow is suppressed throughout all the pH values (symbol of triangle in FIG. 1). Therefore, the essential difference of the capillary according to the present invention from the capillary having a non-treated inner wall and the LPA coated capillary resides in that, in this example, in the capillary according to the present invention, the electrosmosis flow flows from an anode side to a cathode side under an acidic condition, and thus the present invention exhibits the considerable effect shown in the experimental examples described below (in FIG. 1, the symbol of white rhombus is a capillary coated with polybrene, which is an ionic polymer having positive electric charge. The effective length of the capillary is 20 cm).

Furthermore, it exhibits another considerable effect in that the life of the capillary (useful number of use) is remarkably increased by coating plural times the ionic polymer having positive electric charge and the ionic polymer having negative electric charge. The capillary coated plural times is improved in chemical stability against all an acidic solution, an alkaline solution and an aqueous organic solvent. Accordingly, the coating is not easily peeled even when these solvents are used. Moreover, the capillary coated plural times has a large number of theoretical plates, and in particular, exhibits a conspicuous effect in analysis of a basic protein.

EXPERIMENTAL EXAMPLE 1

Capillary Zone Electrophoresis Under Acidic Condition

Figure 2:
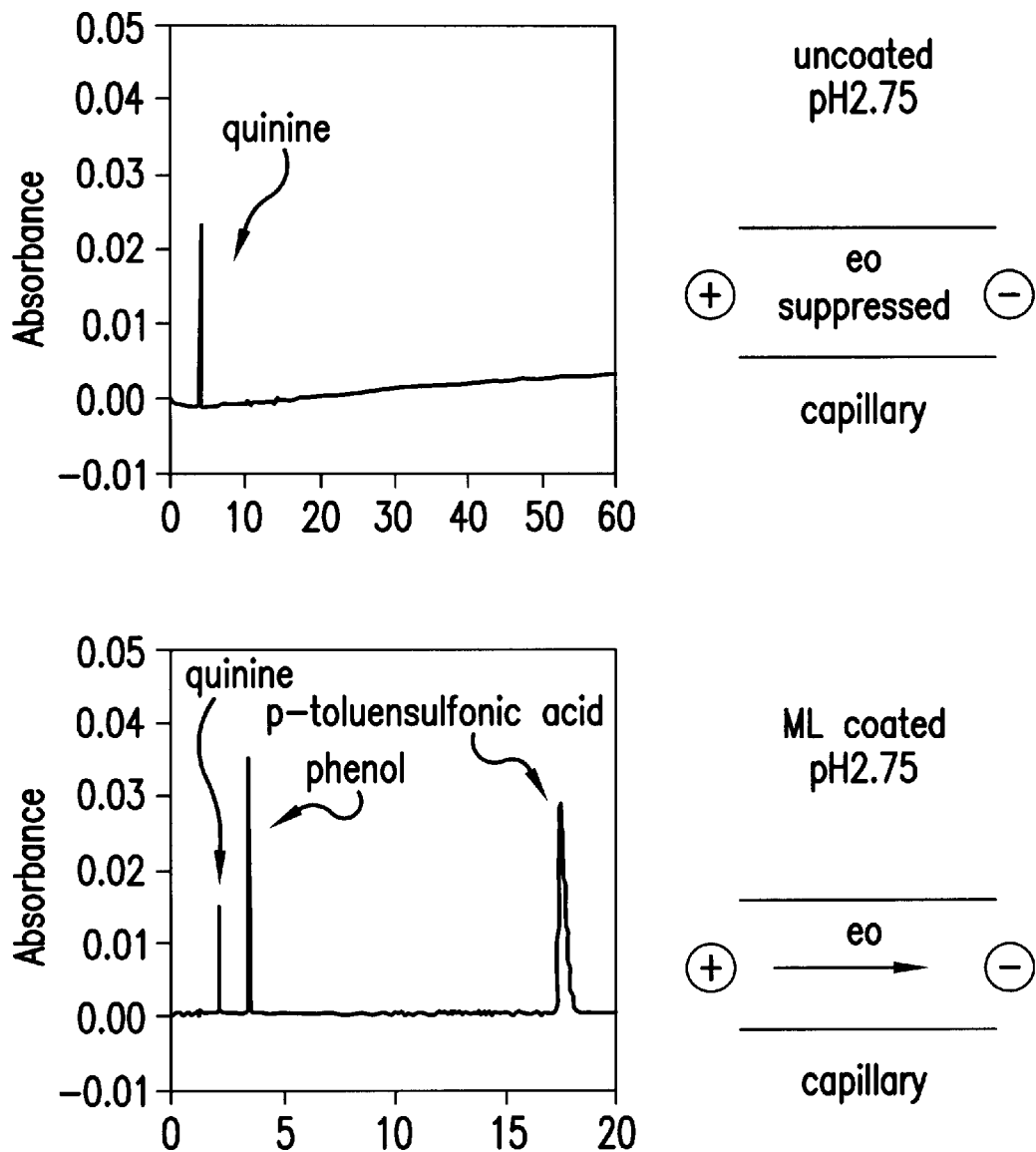
FIG. 2 is a diagram showing capillary zone electrophoresis under an acidic condition. ML coated means a capillary according to the present invention, and uncoated means a capillary having no coating used as control. The upper right figure shows the state in that there is no electrosmosis flow, and the lower right figure shows the state in that an electrosmosis flow is flowing.

An example of capillary zone electrophoresis (hereinafter abbreviated as CZE) under acidic condition is shown in FIG. 2. It is considered that since the electrophoretic solution has pH 2.75, the electrosmosis flow is substantially terminated in a capillary having a non-treated inner wall. As a sample to be analyzed, quinine having positive electric charge at pH 2.75, p-toluene sulfonic acid having negative electric charge at pH 2.75 and neutral phenol were used. In the CZE using the capillary having a non-treated inner wall, only quinine having positive electric charge was detected (upper figure of FIG. 2). Due to the electrosmosis flow being suppressed, neutral phenol and p-toluene sulfonic acid of negative electric charge were not detected. In the capillary according to the present invention, which was obtained in Example 1, since the electrosmosis flow was formed, all the peaks were detected (lower figure of FIG. 2). It is clear from the above that by using the capillary according to the present invention, simultaneous detection of compounds of positive electric charge, negative electric charge and neutrality under an acidic condition, which has been impossible, can be conducted.

EXPERIMENTAL EXAMPLE 2

Micellar Electrokinetic Chromatograph Under Acidic Condition

Figure 3:
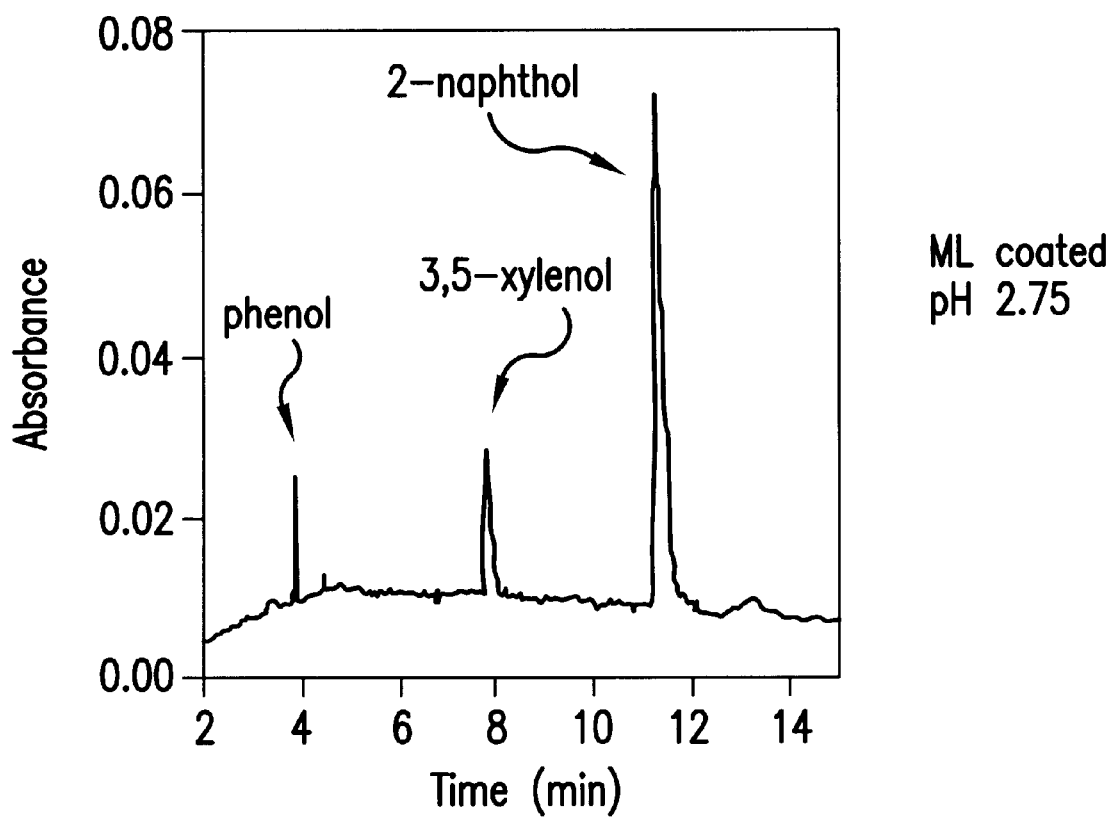
FIG. 3 is a diagram showing micellar electrokinetic chromatography under an acidic condition. ML coated means a capillary according to the present invention.

The micellar electrokinetic chromatograph (hereinafter abbreviated as MEKC) is a mode in that the separation of a compound with no electric charge can be conducted by adding an ionic micellar into an electrophoretic solution. In the MEKC under an acidic condition, since an SDS is adsorbed on the inner wall of the capillary, an electrosmosis flow is slightly formed. A sample having a large capacity (k') ratio is detected at an anode side, and a sample having a small capacity ratio is detected at a cathode side. A sample having the same mobility as the electrosmosis flow in a direction opposite thereto is not detected on any side. Therefore, simultaneous detection is impossible, or a considerably long period of time is required for detecting a sample that can be detected. An experimental example of the MEKC using the capillary obtained in Example 1 under an acidic condition (pH 2.75) is shown in FIG. 3. When phenol, 3,5-xylenol and 2-naphthol were used as a sample, simultaneous detection could be accomplished in a short period of time. Accordingly, simultaneous detection of neutral compounds under an acidic condition could be conducted in a short period of time by the MEKC by using the capillary according to the present invention.

EXPERIMENTAL EXAMPLE 3

Measurement of pKa

In the measurement of pKa using the conventional capillary having a non-treated inner wall, the measurement of a compound having a low pKa value has been difficult. That is, in the capillary having a non-treated inner wall, because the electrosmosis flow becomes small with decreasing pH and is stopped at the last, an error occurs in an acidic region in the capillary electrophoretic method, in which pKa is calculated by obtaining a mobility from the difference between the sample and the electrosmosis flow. Then, the measurement of pKa was conducted by using the capillary according to the present invention obtained in Example 1, in which the constant electrosmosis flow was formed even under an acidic condition. Tryptophan was used as a sample, and the result was compared with the value obtained by Ishihama et al and the value from literature. The results are shown in Table 1 (in the table, ML coated means the capillary according to the present invention, and uncoated means the capillary having no coating used as control).

TABLE 1

Comparison of pKa Value of Trp by CE Method

|  | pKa value of Trp |
|---|---|
| ML coated | 2.38 |
| Uncoated | 2.31 |
| (value measured by Ishihama) |  |
| Value from literature | 2.38 |

Figure 4:
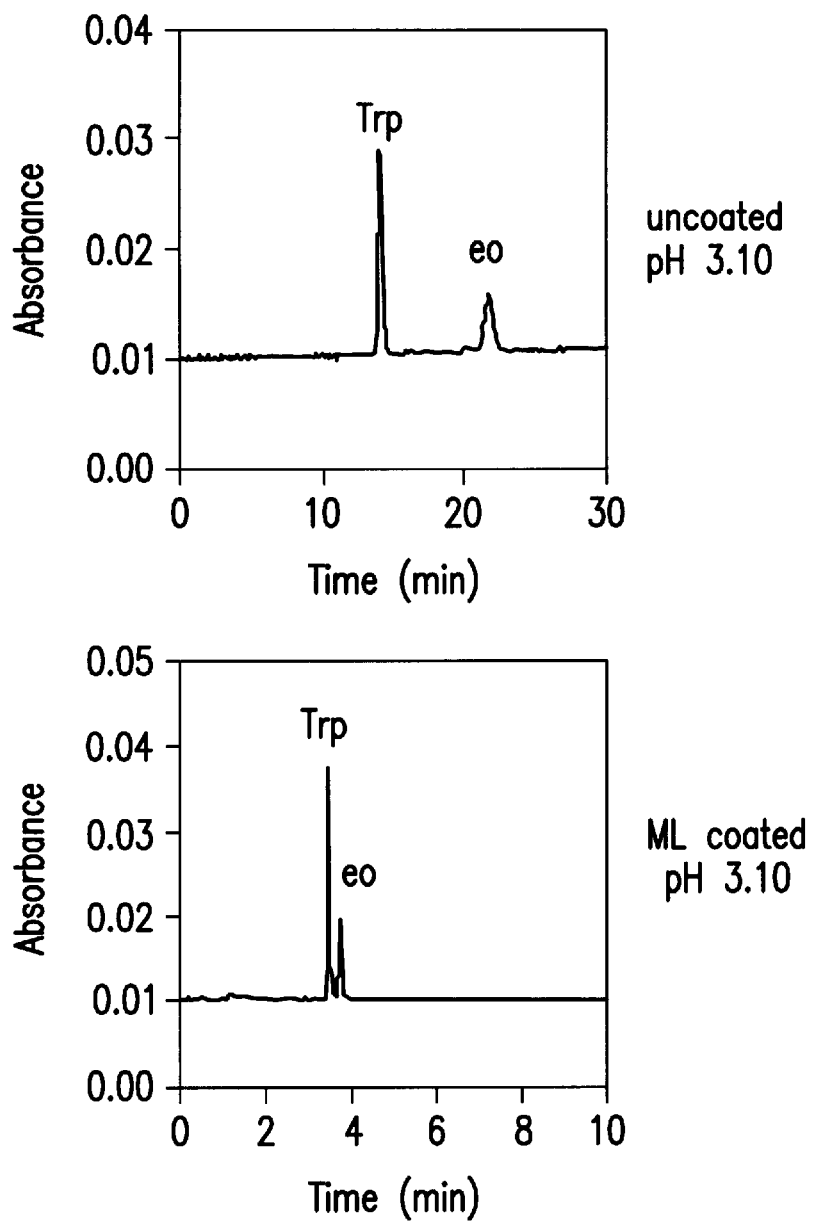
FIG. 4 is a diagram showing the measurement of pKa of tryptophan by a capillary electrophoresis method. ML coated means a capillary according to the present invention, and uncoated means a capillary having no coating used as control.

It is clear from the table that the measurement value using the invention well agrees with the value from literature. An electropherogram at pH 3.10 is shown in FIG. 4. The electrosmosis flow was detected after 20 minutes in the capillary having a non-treated inner wall (upper figure in FIG. 4), but was detected in 4 minutes in the capillary according to the present invention (lower figure in FIG. 4). Because in the capillary according to the present invention, the peak of the electrosmosis flow is detected at substantially the same time with good reproducibility at pH 3.10 or less, it is considered that the measurement of pKa of a compound having a lower pKa can be precisely conducted. Furthermore, it is clear from FIG. 4 that the capillary according to the present invention realizes reduction in analysis time under an acidic condition.

EXPERIMENTAL EXAMPLE 3

A durability test on continuous use was conducted by using the capillary obtained in Example 2. When evaluation was conducted by measuring the electrosmosis flow at pH 3, the coating was peeled after about 20 times in the capillary having coated one layer of polybrene used as control, whereas the capillary of Example 2 was stable after 593 times use. It is considered that this is because the ionic mutual interaction between the heparin fraction and polybrene is larger than the ionic mutual interaction between the silanol group on the inner wall of the capillary and polybrene.

EXAMPLE

The present invention will be described in detail with reference to Examples below, but the present invention is not limited to them.

Example 1

Contamination on an inner wall of a capillary was first removed, and in order to completely dissociate a silanol group it was rinsed with 1N NaOH for 30 minutes and then with water for 15 minutes by using a rinsing function of a capillary electrophoresis apparatus (Beckman P/ACE 2100). It was then rinsed with a 0.4% polybrene aqueous solution for 30 minutes, followed by being allowed to stand over night. After standing over night, it was confirmed that the electrosmosis flow (eo) had been reversed by using a marker (formamide diluted solution) it was rinsed with a 5% polybrene aqueous solution for 5 minutes, followed by immediately rinsing with 2% dextran sulfate aqueous solution for 10 minutes, to produce a capillary according to the present invention.

Example 2

Contamination on an inner wall of a capillary was first removed, and in order to completely dissociate a silanol group, it was rinsed with 1N NaOH for 30 minutes and then with water for 15 minutes by using a rinsing function of a capillary electrophoresis apparatus (Beckman P/ACE 2100). It was then rinsed with a 10% polybrene aqueous solution, a 3% heparin fraction III (available from WAKO Co., Ltd.), and a 10% polybrene solution in this order for 15 minutes, so as to produce a capillary according to the present invention.

What is claimed is:

1. An electrophoresis capillary comprising (A) an ionic polymer layer selected from the group consisting of polybrene, chitosan and diethylaminoethyldextran and (B) a negatively charged ionic polymer layer selected from the group consisting of dextran sulfate, heparin, heparin sulfate, hyaluronic acid, chondroitin sulfate, keratan sulfate, polygalacturonic acid, arginic acid and teikronic acid, wherein said (A) ionic polymer layer is adsorbed on an inner wall of said capillary tubing and said (B) negatively charged ionic polymer layer is coated on said (A) ionic polymer layer to form an innermost wall of the capillary.

2. The capillary of claim 1, with the positions of layers (A) and (B) interchanged.

3. A process for producing the electrophoresis capillary of claim 1, comprising adsorbing on the inner wall of the capillary, an ionic polymer having a positive electric charge and coating on said ionic polymer having a positive electric charge an ionic polymer having a negative charge.

4. The process for producing a capillary as claimed in claim 3, comprising the step of firstly rinsing the capillary with a strong alkali solution before making it adsorb the ionic polymer having positive electric charge.

5. The capillary as claimed in claim 1, wherein the first ionic polymer layer or the second ionic polymer layer is an innermost layer.

6. The capillary as claimed in claim 1, wherein the capillary has an inner diameter of 50 to 100 $\mu$m.

7. The capillary as claimed in claim 1, or 2 wherein each layer is coated twice or more.

8. A method of conducting capillary electrophoresis which comprises conducting electrophoresis with a capillary having absorbed on an inner wall of the capillary, a first layer of an ionic polymer having positive electric charge selected from the group consisting of polybrene, chitosan or diethylaminoethyldextran, and a second layer of an ionic polymer having negative electric charge selected from the group consisting of dextran sulfate, heparin, heparin sulfate, hyaluronic acid, chondroitin sulfate, keratan sulfate, polygalacturonic acid, arginic acid or teikronic acid, alternately, wherein the first layer is coated on the second layer or the second layer is coated on the first layer.

9. The method of claim 8, wherein the capillary has a first layer or second layer that is an innermost layer next to the inner wall of the capillary.

10. The method of claim 8, wherein the capillary has an inner diameter of 50 to 100 $\mu$m.

11. The method of claim 8, wherein the capillary has layers that are coated twice or more.

* * * * *

(12) EX PARTE REEXAMINATION CERTIFICATE (6207th)
United States Patent
Katayama et al.

(10) Number: US 6,586,065 C1
(45) Certificate Issued: Apr. 22, 2008

(54) CAPILLARY HAVING COATED INNER WALL

(75) Inventors: Hiroyuki Katayama, Ibaraki (JP); Yasushi Ishihama, Ibaraki (JP)

(73) Assignee: Eisai Co., Ltd., Bunkyo-Ku, Tokyo (JP)

Reexamination Request:
No. 90/006,927, Jan. 30, 2004

Reexamination Certificate for:
Patent No.: 6,586,065
Issued: Jul. 1, 2003
Appl. No.: 09/319,043
Filed: Jun. 1, 1999

(22) PCT Filed: Dec. 3, 1997

(86) PCT No.: PCT/JP97/04422
§ 371 (c)(1),
(2), (4) Date: Jun. 1, 1999

(87) PCT Pub. No.: WO98/25137
PCT Pub. Date: Jun. 11, 1998

(30) Foreign Application Priority Data
Dec. 3, 1996 (JP) .............................. 8-323021

(51) Int. Cl.
*G01N 27/447* (2006.01)

(52) U.S. Cl. .................. 428/36.9; 156/272.2; 156/278; 204/454; 428/34.7; 428/420

(58) Field of Classification Search ...................... None
See application file for complete search history.

(56) References Cited

U.S. PATENT DOCUMENTS 5,611,903 A * 3/1997 Janssens et al. ............ 204/454

FOREIGN PATENT DOCUMENTS

JP 09-105739 * 4/1997

* cited by examiner

*Primary Examiner*—Alan Diamond

(57) ABSTRACT

It is to provide a capillary having adsorbed a polymer.

A capillary having absorbed on an inner wall of the capillary, an ionic polymer having positive electric charge and an ionic polymer having negative electric charge alternately, and a process for producing the same.

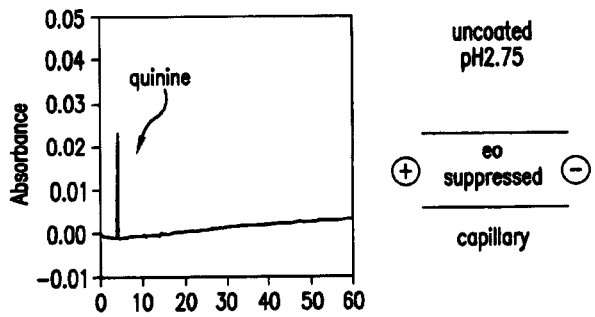
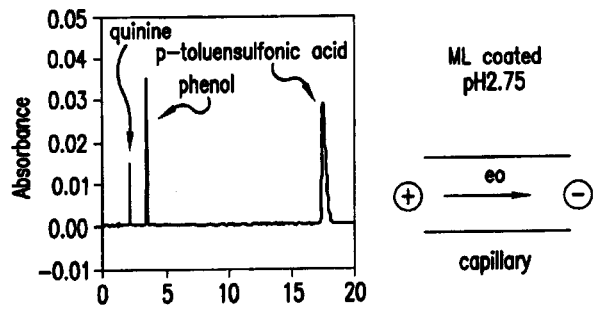

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1–7 and 9 are cancelled.

Claims 8, 10 and 11 are determined to be patentable as amended.

New claims 12–29 are added and determined to be patentable.

8. A method of conducting capillary electrophoresis which comprises conducting electrophoresis with a capillary [having absorbed on an inner wall of the capillary,] *wherein the capillary comprises at least:*
   a first layer of an ionic polymer having positive electric charge selected from *at least one of* the group consisting of polybrene, chitosan [or] *and* diethylaminoethyldextran *absorbed on an inner wall of the capillary,* [and]
   a second layer of an ionic polymer having negative electric charge selected from *at least one of* the group consisting of dextran sulfate, heparin, heparin sulfate, hyaluronic acid, chondroitin sulfate, keratan sulfate, polygalacturonic acid, arginic acid [or] *and* teikronic acid *coated on the first layer, and*
   [alternately, wherein the first layer is coated on the second layer or the second is coated on the first layer] *a third layer of an ionic polymer having positive electric charge selected from at least one of the group consisting of polybrene, chitosan and diethylaminoethyldextran coated on the second layer.*

10. The method of claim 8, wherein the *uncoated* capillary has an inner diameter of 50 to 100 μm.

11. The method of claim 8, wherein the [capillary has] positive *and negative charge* layers [that] are *each* coated [twice] *alternately two times* or more.

12. *The method of claim 11, wherein the uncoated capillary has an inner diameter of 50 to 100 μm.*

13. *An electrophoresis capillary which comprises:*
   *at least a first layer of an ionic polymer having positive electric charge selected from at least one of the group consisting of polybrene, chitosan and diethylaminoethyldextran,*
   *at least a second layer of an ionic polymer having negative electric charge selected from at least one of the group consisting of dextran sulfate, heparin, heparin sulfate, hyaluronic acid, chondroitin sulfate, keratan sulfate, polygalacturonic acid, arginic acid and teikronic acid coated on the first layer,*
   *wherein said first ionic polymer layer is adsorbed on an inner wall of said capillary and said second negatively charged ionic polymer layer is coated on said first ionic polymer layer to form an innermost wall of the capillary, and*
   *wherein at least one of said first and second layers is coated alternately two or more times.*

14. *A method for producing an electrophoresis capillary, which comprises at least:*
   *a first layer of an ionic polymer having positive electric charge selected from at least one of the group consisting of polybrene, chitosan and diethylaminoethyldextran, and*
   *a second layer of an ionic polymer having negative electric charge selected from at least one of the group consisting of dextran sulfate, heparin, heparin sulfate, hyaluronic acid, chondroitin sulfate, keratan sulfate, polygalacturonic acid, arginic acid and teikronic acid,*
   *wherein said first ionic polymer layer is adsorbed on an inner wall of said capillary and said second negatively charged ionic polymer layer is coated on said first ionic polymer layer,*
   *said method comprising the steps of:*
   *(1) adsorbing on the inner wall of the capillary having been rinsed with a strong alkali solution, the first layer of an ionic polymer having a positive electric charge, and*
   *(2) coating on said first layer the second layer of an ionic polymer having a negative electric charge,*
   *wherein at least one of said first and second layers is coated alternately two or more times, and either the first or second layer forms the innermost wall of the capillary.*

15. *The method as claimed in claim 14, wherein the uncoated capillary has an inner diameter of 50 to 100 μm.*

16. *A method of conducting capillary electrophoresis which comprises conducting electrophoresis with an electrophoresis capillary which comprises:*
   *at least a first layer of an ionic polymer having positive electric charge selected from at least one of the group consisting of polybrene, chitosan and diethylaminoethyldextran,*
   *at least a second layer of an ionic polymer having negative electric charge selected from at least one of the group consisting of dextran sulfate, heparin, heparin sulfate, hyaluronic acid, chondroitin sulfate, keratan sulfate, polygalacturonic acid, arginic acid and teikronic acid,*
   *and wherein said first ionic polymer layer is adsorbed on an inner wall of said capillary and said second negatively charged ionic polymer layer is coated on said first ionic polymer layer,*
   *wherein at least one of said first and second layers is coated alternately two or more times, and either the first or second layer forms the innermost wall of the capillary.*

17. *A method of conducting capillary electrophoresis which comprises conducting electrophoresis with a capillary which comprises:*
   *a first layer of an ionic polymer having positive electric charge selected from at least one of the group consisting of polybrene, chitosan and diethylaminoethyldextran, and*
   *a second layer of an ionic polymer having negative electric charge selected from at least one of the group consisting of dextran sulfate, heparin, heparin sulfate, hyaluronic acid, chondroitin sulfate, keratan sulfate, polygalacturonic acid, arginic acid and teikronic acid,*
   *wherein said first ionic polymer layer is adsorbed on an inner wall of said capillary and said second negatively* charged ionic polymer layer is coated on said first ionic polymer layer, said capillary formed by a method comprising the steps of:
(1) adsorbing on the inner wall of the capillary having been rinsed with a strong alkali solution, the first layer of an ionic polymer having a positive electric charge, and
(2) coating on said first layer the second layer of an ionic polymer having a negative electric charge, and wherein at least one of said first and second layers is coated alternately two or more times.

18. The method of claim 16, wherein the uncoated capillary has an inner diameter of 50 to 100 μm.

19. The electrophoresis capillary of claim 13, wherein the uncoated capillary has an inner diameter of 50 to 100 μm.

20. An electrophoresis capillary which comprises at least:

a first layer of an ionic polymer having positive electric charge selected from at least one of the group consisting of polybrene, chitosan and diethylaminoethyldextran, and a second layer of an ionic polymer having negative electric charge selected from at least one of the group consisting of dextran sulfate, heparin, heparin sulfate, hyaluronic acid, chondroitin sulfate, keratan sulfate, polygalacturonic acid, arginic acid and teikronic acid, wherein said first ionic polymer layer is adsorbed on an inner wall of said capillary and said second negatively charged ionic polymer layer is coated on said first ionic polymer layer, said capillary being formed by the method of:
(1) adsorbing on the inner wall of the capillary having been rinsed with a strong alkali solution, the first layer of an ionic polymer having a positive electric charge, and
(2) coating on said first layer the second layer of an ionic polymer having a negative electric charge, wherein at least one of said first and second layers is coated alternately two or more times, and either the first or second layer forms the innermost wall of the capillary.

21. The method of claim 14, wherein said strong alkali is selected from the group consisting of sodium hydroxide and potassium hydroxide.

22. An electrophoresis capillary comprising:

a first layer of an ionic polymer having positive electric charge selected from at least one of the group consisting of polybrene, chitosan and diethylaminoethyldextran adsorbed on the inner wall of the capillary, a second layer of an ionic polymer having negative electric charge selected from at least one of the group consisting of dextran sulfate, heparin, heparin sulfate, hyaluronic acid, chondroitin sulfate, keratan sulfate, polygalacturonic acid, arginic acid and teikronic acid coated on the first layer, and a third layer of an ionic polymer having positive electric charge selected from at least one of the group consisting of polybrene, chitosan and diethylaminoethyldextran coated on said second layer, wherein said ionic polymer layer of said third layer having positive electric charge forms an innermost wall of the capillary.

23. The capillary as claimed in claim 22, wherein the uncoated capillary has an inner diameter of 50 to 100 μm.

24. The capillary as claimed in claim 22, wherein each layer having the positive or negative charge is coated alternately two times or more.

25. An electrophoresis capillary comprising:

a first layer of an ionic polymer having positive electric charge selected from at least one of the group consisting of polybrene, chitosan and diethylaminoethyldextran adsorbed on the inner wall of the capillary, a second layer of an ionic polymer having negative electric charged selected from at least one of the group consisting of dextran sulfate, heparin, heparin sulfate, hyaluronic acid, chondroitin sulfate, keratan sulfate, polygalacturonic acid, arginic acid and teikronic acid coated on the first layer, said ionic polymer layer having positive charge and said ionic polymer layer having negative charge being coated alternately twice or more, whereby the innermost layer of said capillary is said negatively charged layer.

26. A method for producing an electrophoresis capillary comprising:

a first layer of an ionic polymer having positive electric charge selected from at least one of the group consisting of polybrene, chitosan and diethylaminoethyldextran adsorbed on an inner wall of the capillary, a second layer of an ionic polymer having negative electric charge selected from at least one of the group consisting of dextran sulfate, heparin, heparin sulfate, hyaluronic acid, chondroitin sulfate, keratan sulfate, polygalacturonic acid, arginic acid and teikronic acid coated on said first layer, and a third layer of an ionic polymer having positive electric charge selected from at least one of the group consisting of polybrene, chitosan and diethylaminoethyldextran coated on said second layer, whereby the innermost layer of said capillary is said third layer, comprising the steps of:
(1) adsorbing on the inner wall of the capillary, the first layer of an ionic polymer having a positive electric charge,
(2) coating on said first layer said second layer of an ionic polymer having a negative electric charge, and
(3) coating on said second layer said third layer of an ionic polymer having a positive electric charge.

27. The method as claimed in claim 26, further comprising the step of rinsing the capillary with a strong alkali solution before making it adsorb the first layer.

28. The method as claimed in claim 27, wherein said strong alkali is selected from the group consisting of sodium hydroxide and potassium hydroxide.

29. The method of conducting capillary electrophoresis of claim 17, wherein said strong alkali is selected from the group consisting of sodium hydroxide and potassium hydroxide.

* * * * *